United States Patent

Akimoto et al.

[11] Patent Number: 4,592,907
[45] Date of Patent: Jun. 3, 1986

[54] HAIR-RINSE LIQUID WITH PEARLY LUSTER

[75] Inventors: Shin-ichi Akimoto, Machida; Akinori Suginaka, Chigasaki, both of Japan

[73] Assignee: Nippon Oil and Fats Co., Ltd., Tokyo, Japan

[21] Appl. No.: 713,980

[22] Filed: Mar. 20, 1985

[30] Foreign Application Priority Data

Apr. 16, 1984 [JP] Japan ................................ 59-76199

[51] Int. Cl.$^4$ .............................................. A61K 7/06
[52] U.S. Cl. ...................................... 424/70; 514/880
[58] Field of Search ........................................ 424/70

[56] References Cited

U.S. PATENT DOCUMENTS

| | | | |
|---|---|---|---|
| Re. 30,874 | 3/1982 | Dasher et al. | 132/7 |
| 4,096,243 | 6/1978 | Feinland et al. | 424/70 |
| 4,165,369 | 8/1979 | Watanabe et al. | 424/70 |
| 4,187,289 | 2/1980 | Eckhardt | 424/70 |
| 4,438,096 | 3/1984 | Preston | 424/70 |

FOREIGN PATENT DOCUMENTS

| | | | |
|---|---|---|---|
| 2452505 | 11/1980 | France | 424/70 |
| 0033447 | 3/1980 | Japan | 514/786 |
| 0079314 | 6/1980 | Japan | 424/70 |
| 0022717 | 3/1981 | Japan | 424/70 |
| 155298 | 12/1981 | Japan | 424/70 |
| 0206605 | 6/1982 | Japan | 424/70 |

OTHER PUBLICATIONS

Quack, Cosmetics and Toiletries, 2/1976, vol. 91, pp. 35, 36, 38, 40, 43, 44, 46, 48, 50, 52.
Cannell, Cosmetic and Toiletries, 3/1979, vol. 94, pp. 29 to 3.
Schoenberg et al., Cosmetics and Toiletries, 3/1979, vol. 94, pp. 57 to 59, 60, 63, 64.

Primary Examiner—Dale R. Ore
Attorney, Agent, or Firm—Flynn, Thiel, Boutell & Tanis

[57] ABSTRACT

It is proposed a hair-rinse liquid having pearly luster, which includes the following four components A to D, namely:

component A: a cationic surface active agent expressed by the general formula (I), as given below;
component B: an amine oxide represented by the general formula (II), as given also in below;
component C: an amino acid having an isoelectric point not higher than 7 and
component D: a salt of an alkali metal or alkaline earth metal.

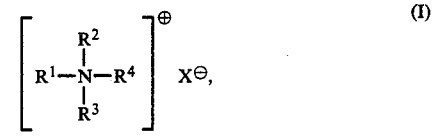

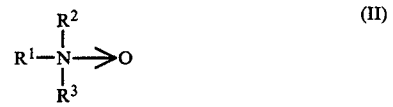

In the above formulae (I) and (II), $R^1$, $R^2$, $R^3$ and $R^4$ represent each a hydrocarbon group or a hydroxy alkyl group having 1-24 carbon atoms, which may be identical or different with each other, and the sum of the total carbon atoms in each formula should lie within the range of 16–45 and X denotes a halogen atom.

7 Claims, No Drawings

HAIR-RINSE LIQUID WITH PEARLY LUSTER

BACKGROUND OF THE INVENTION

1. Field of the Invention

The present invention relates to a hair-rinse liquid and, in particular, to a hair-rinse liquid with pearly luster.

2. Description of the Prior Art

A hair-rinse liquid functions in softening the hair to improve smooth combing, preventing electrostatic charge, rendering the hair supple and lustrous and protecting the hair surfaces. Cationic surface active agents are known to satisfy these requirements. Thus, conventional hair-rinse liquids contain, as the main component, a cationic surface active agent in addition to, such as, moisture-keeping agent, oil or fat and so on.

A hair-rinse liquid containing a cationic surface active agent as the main component is very difficult to make with a pearly luster, in order to obtain a pleasing appearance thereof. Accordingly, such a hair-rinse liquid has in most cases been offered in the market with a transparent or turbid appearance.

While there have been brought into the market products exhibiting a weak pearly luster, they are not only unsatisfactory in their pearliness but also difficult to maintain controlled manufacturing thereof, since they are prepared under complicated procedures with the use of a "pearliness-imparting agent" designated for shampoo, such as ethylene glycol distearate and the like. Moreover, hair-rinse liquids containing a cationic surface active agent as the main component have a defect of causing an irritative action upon skin.

SUMMARY OF THE INVENTION

An object of the present invention is to eliminate the above defects of the conventional hair-rinse liquids.

Another object of the invention is to provide a hair-rinse liquid having a superior rinsing effect and exhibiting a beautiful pearl-like luster with little irritating action.

A further object of the invention is to provide a hair-rinse liquid consisting of cationic surface active agent, amine oxide, amino acid and metal salt of specific kinds.

DETAILED DESCRIPTION OF THE INVENTION

A hair-rinse liquid with pearly luster according to the present invention comprises:

Component A: a cationic surface active agent expressed by the general formula (I), as given below, Component B: an amine oxide represented by the general formula (II), as given also in below, Component C: an amino acid having an isoelectric point not higher than 7 and Component D: a salt of an alkali metal or alkaline earth metal, wherein the weight proportion A:B:C:D corresponds to 1:[0.1–10]:[0.01–2]:[0.01–2].

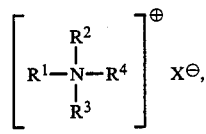

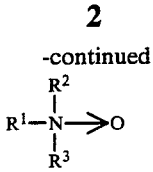

In the above formulae (I) and (II), $R^1$, $R^2$, $R^3$ and $R^4$ represent each a hydrocarbon group or hydroxy alkyl group having 1–24 carbon atoms, which may be identical to or different from each other, wherein the sum of the total carbon atoms in each formula should lie within the range of 16–45, and X denotes a halogen atom.

As the hydrocarbon group having 1–24 carbon atoms represented by $R^1$, $R^2$, $R^3$ and $R^4$ in the above general formulae (I) and (II) may be exemplified, such as, methyl, ethyl, propyl, isopropyl, allyl, butyl, isobutyl, tert-butyl, amyl, isoamyl, hexyl, heptyl, octyl, 2-ethylhexyl, nonyl, decyl, undecyl, lauryl, tridecyl, myristyl, cetyl, isocetyl, stearyl, isostearyl, oleyl, octyldodecyl, behenyl, docosenyl, decyltetradecyl, benzyl and so on. As the hydroxylakyl group, there may be enumerated, for example, hydroxyethyl, hydroxypropyl, hydroxybutyl, 2,3-dihydroxypropyl and so on. Halogen atoms of X in the formula (I) may include, for example, chlorine, bromine and so on.

Suitable examples of the cationic surface active agent of component A include, for example, trimethyl cetylammonium chloride, trimethyl stearylammonium chloride, trimethyl behenylammonium chloride, trimethyl docosenylammonium chloride, dimethyl dicetylammonium chloride, dimethyl distearylammonium chloride, trimethyl octyldodecylammonium chloride, trimethyl decyltetradecylammonium chloride and so on.

As preferable amine oxide of the component B, there may be enumerated, for example, N,N-dimethyl cetylamine oxide, N,N-dimethyl stearylamine oxide, N,N-di-(2-hydroxyethyl)stearylamine oxide, N-methyl distearylamine oxide, N,N-dimethyl behenylamine oxide, N,N-dimethyl docosenylamine oxide, N,N-dimethyl octyldodecylamine oxide, N,N-dimethyl decyltetradecylamine oxide and so on.

As the amino acid having an isoelectric point not higher than 7 as the component C, there may be exemplified glycine, alanine, valine, leucine, isoleucine, serine, threonine, phenylalanine, tyrosine, triptophane, cysteine, cystine, methionine, proline, hydroxyproline, asparaginic acid, glutamic acid, asparagine, glutamine and so on.

As the salt of alkali metal or alkaline earth metal for the component D, for example, salts of strong acid, such as, hydrochloric acid, sulfuric acid and phosphoric acid with sodium, potassium, magnesium and calcium, and alums can be used.

The sum of total number of carbon atoms in each of the general formulae (I) and (II) should be limited in the above mentioned range, since the rinsing action will be lost due to the excessive high water solubility when the total sum is short of 16, whereas in case it exceeds 45, the water-dispersibility becomes low.

The isoelectric point of the amino acid should be limited so as not to exceed over 7, since an amino acid having an isoelectric point higher than 7 may not be dissolved in the hair-rinse liquid and may form a deposit of solid matter.

The hair-rinse liquid according to the present invention contains as its essential components a cationic surface active agent expressed by the general formula (I)

for the component A, an amine oxide represented by the general formula (II) for the component B, an amino acid having an isoelectric point not higher than 7 for the component C and a salt of alkali or alkaline earth metal for the component D. Here, the mixing proportion in weight basis of A:B:C:D should correspond to 1:0.1–10:0.01–2:0.01–2, and preferably 1:0.5–2:0.05–1:0.05–1.

Hair-rinse liquids according to the present invention may contain other components employed usually in the conventional hair-rinse liquids, for example, flavors, coloring agents, nutrients, oily substances, thickners, refrigerants and so on. These hair-rinse liquids can be put in the market in a form dispersed in a solvent, such as, water, ethanol etc. The range of content of the component A may be from 0.5 to 10%, preferably from 1 to 7% by weight.

The hair-rinse liquid according to the present invention obtained as above gives off a pearly luster capable of being maintained on storage at every temperature from warm to cold conditions for long periods of time without losing its initial appearance. This hair-rinse liquid can be applied to the hair by hand without suffering from irritative action upon the skin and hair. It brings forth softening of hair, smoothness in combing, prevention of electrostatic charge, a glossy and supple appearance of hair and protection of hair surfaces.

In the present invention, it is essential that the four components, namely, a cationic surface active agent of general formula (I), an amine oxide of general formula (II), an amino acid having an isoelectric point not higher than 7 and an alkali or alkaline earth metal salt, are present each in the prescribed amount, since a lack of any one of these will cause disappearance of the pearly luster and appearance of irritative action.

While the reason why the hair-rinse liquid according to the present invention brings forth pearly luster is not yet clear, it is supposed to be due to deposition of a salt of the amine oxide with the amino acid.

For the cationic surface active agent of general formula (I) or for the amine oxide of general formula (II), it is possible to use one or more compounds having radicals of $R^1$–$R^4$ in any combination. For the amino acid having isoelectric point not higher than 7 or for the alkali or alkaline earth metal salt, it is also possible to employ one or more compounds.

According to the present invention, a hair-rinse liquid exhibiting pearly luster without irritating action can be obtained, since it is constituted from the components of cationic surface active agent, amine oxide, amino acid and alkali or alkaline earth metal salt of special kinds. The hair-rinse liquid according to the present invention offers superior effects, such as, attainment of softening of hair and smooth combing, prevention of electrostatic charge, protection of the hair surfaces, making hair supple and lustrous.

DESCRIPTION OF THE PREFERRED EMBODIMENTS

Below, the invention is further explained by way of Examples, in which all % composition values are given on a weight basis.

EXAMPLE 1

Each composition recited in Table 1, the rest of the amount being deionized water, were added together and heated to 70° C. to form a homogeneous liquid. This liquid was divided into two parts, for which observation of their appearance was made after they had been cooled to 20° C. These two samples were then stored each in a constant temperature bath of 40° C. or 0° C. respectively for 90 days and the change in the appearance was inspected. The results are summarized in Table 1.

From the results given in Table 1, it is seen that the hair-rinse liquids of Comparison Products either did not exhibit pearly luster or did show disappearance of the pearly luster during storage, whereas the samples according to the present invention maintained a stable pearly appearance.

TABLE 1

| Test No. | A (Cation. Surfactant) (%) | B (Amine Oxide) (%) | C (Amino Acid) (%) | D (Salt) (%) | Other (%) | Pearly Luster*** Direct. after | At 40° C. | At 0° C. |
|---|---|---|---|---|---|---|---|---|
| 1* | $[C_{16}H_{33}\underset{\underset{CH_3}{\mid}}{\overset{\overset{CH_3}{\mid}}{N}}-CH_3]^+Cl^-$ (2.0) | $C_{22}H_{45}\underset{\underset{CH_3}{\mid}}{\overset{\overset{CH_3}{\mid}}{N}}\longrightarrow O$ (2.0) | Asparaginic acid (0.4) | NaCl (0.2) | — | O | O | O |
| 2* | $[C_{18}H_{37}\underset{\underset{CH_3}{\mid}}{\overset{\overset{CH_3}{\mid}}{N}}-CH_3]^+Cl^-$ (2.2) | $C_{18}H_{37}\underset{\underset{CH_3}{\mid}}{\overset{\overset{CH_3}{\mid}}{N}}\longrightarrow O$ (1.8) | Glutamic acid (0.3) | MgSO$_4$ (0.1) | — | O | O | O |
| 3* | $[C_{22}H_{45}\underset{\underset{CH_3}{\mid}}{\overset{\overset{CH_3}{\mid}}{N}}-CH_3]^+Cl^-$ (1.8) | $C_{18}H_{37}\underset{\underset{CH_3}{\mid}}{\overset{\overset{CH_3}{\mid}}{N}}\longrightarrow O$ (3.0) | Glutamic acid (0.4) Glycine (0.1) | KCl (0.2) | — | O | O | O |

TABLE 1-continued

| Test No. | A (Cation. Surfactant) (%) | B (Amine Oxide) (%) | C (Amino Acid) (%) | D (Salt) (%) | Other (%) | Pearly Luster*** Direct. after | At 40° C. | At 0° C. |
|---|---|---|---|---|---|---|---|---|
| 4* | $[C_{18}H_{37}\underset{CH_3}{\overset{CH_3}{N}}-CH_2C_6H_5]^+Cl^-$ (1.5) | $C_{18}H_{37}\underset{CH_2CH_2OH}{\overset{CH_2CH_2OH}{N}}\longrightarrow O$ (2.8) | Asparaginic acid (0.2) | Na$_2$SO$_4$ (0.4) | — | O | O | O |
| 5* | $[C_{22}H_{45}\underset{CH_3}{\overset{CH_3}{N}}-CH_3]^+Cl^-$ (1.6) | $C_{18}H_{37}\underset{CH_3}{\overset{CH_3}{N}}\longrightarrow O$ (1.0)<br><br>$C_{18}H_{37}\underset{CH_3}{\overset{C_{18}H_{37}}{N}}\longrightarrow O$ (0.5) | Asparaginic acid (0.2) | Na$_2$SO$_4$ (0.3) | Ethanol (8.0) | O | O | O |
| 6* | $[C_{22}H_{42}\underset{CH_3}{\overset{CH_3}{N}}-CH_3]^+Cl^-$ (3.0) | $C_{18}H_{37}\underset{CH_3}{\overset{CH_3}{N}}\longrightarrow O$ (1.0)<br><br>$C_{16}H_{33}\underset{CH_3}{\overset{CH_3}{N}}\longrightarrow O$ (0.7) | Glutamic acid (0.1) | K$_2$HPO$_4$ (0.1)<br>KCl (0.1) | — | O | O | O |
| 7** | Same as that of No. 2 | Same as that of No. 2 | Same as No. 2 | — | — | Δ | X | Δ |
| 8** | Same as that of No. 2 | Same as that of No. 2 | — | Same as No. 2 | — | Δ | X | Δ |
| 9** | Same as that of No. 2 | — | Same as No. 2 | Same as No. 2 | — | X | X | X |
| 10** | — | Same as that of No. 2 | Same as No. 2 | Same as No. 2 | — | Δ | X | Δ |
| 11** | Same as that of No. 3 | Same as that of No. 3 | Same as No. 3 | — | Ethyleneglycol distearate (1.0) | Δ | Δ | X |
| 12** | Same as that of No. 3 | Same as that of No. 3 | — | Same as No. 3 | Same as the above | Δ | Δ | X |
| 13** | Same as that of No. 3 | — | Same as No. 3 | Same as No. 3 | Same as the above | X | Δ | X |
| 14** | — | Same as that of No. 3 | Same as No. 3 | Same as No. 3 | Same as the above | Δ | Δ | X |

*Samples according to the present invention
**Samples of Comparison Products
***Evaluation of pearly luster: O: Luster of pearly appearance; Δ: Weak pearly luster; X: No pearly luster

EXAMPLE 2

A pearly hair-rinse liquid was formulated by the following recipe:

| | |
|---|---|
| $\left[C_{18}H_{37}-\underset{CH_3}{\overset{C_{18}H_{37}}{N}}-CH_3\right]^{\oplus} Cl^{\ominus}$ | 1.6% |
| $C_{18}H_{37}-\underset{CH_2CH_2OH}{\overset{CH_2CH_2OH}{N}}\longrightarrow O$ | 2.5% |
| Asparaginic acid | 0.3% |
| NaCl | 0.4% |
| Color, flavor and antiseptic | adequate amount |
| Deionized water | 95.2% |

The hair-rinse liquid obtained as above exhibited a pearly luster directly after the formulation and no change in the appearance was recognized after storage for 90 days at room temperature. It possessed almost no irritative action and the hair rinsed with this liquid became soft, supple and sufficiently lustrous.

EXAMPLE 3

A pearly hair-rinse liquid was formulated by the following recipe:

| | |
|---|---|
| $\left[\begin{array}{c} CH_3 \\ | \\ C_{22}H_{45}-N-CH_3 \\ | \\ CH_3 \end{array}\right]^{\oplus} Cl^{\ominus}$ | 2.8% |
| $\begin{array}{c} CH_3 \\ | \\ C_{18}H_{37}-N \longrightarrow O \\ | \\ CH_3 \end{array}$ | 3.2% |
| Glutamic acid | 0.4% |
| $Na_2SO_4$ | 0.6% |
| Color, flavor and antiseptic | adequate amount |
| Deionized water | 93.0% |

The hair-rinse liquid obtained as above exhibited a pearly luster directly after the formulation and no change in the appearance was recognized after storage for 90 days at room temperature. It possessed almost no irritative action and the hair rinsed with this liquid became soft, supple and sufficiently lustrous.

EXAMPLE 4

A pearly hair-rinse liquid was formulated by the following recipe:

| | |
|---|---|
| $\left[\begin{array}{c} CH_3 \\ | \\ C_{22}H_{45}-N-CH_3 \\ | \\ CH_3 \end{array}\right]^{\oplus} Cl^{\ominus}$ | 2.26% |
| $\begin{array}{c} CH_3 \\ | \\ C_{18}H_{37}-N \longrightarrow O \\ | \\ CH_3 \end{array}$ | 2.63% |
| $C_{18}H_{37}O(C_3H_6O)_{35}(C_2H_4O)_3H$ | 1.00% |
| Glutamic acid | 0.30% |
| $Na_2SO_4$ | 0.55% |
| Color, flavor and antiseptic | adequate amount |
| Deionized water | 93.26% |

The so obtained hair-rinse liquid exhibited a pearly luster directly after the formulation and no change in the appearance was recognized after storage for 150 days at 0° C. or at 40° C. in constant temperature bath. It revealed almost no irritative action and the hair rinsed with this liquid became soft, supple and sufficiently lustrous.

EXAMPLE 5

A pearly hair-rinse liquid was formulated by the following recipe:

| | |
|---|---|
| $\left[\begin{array}{c} CH_3 \\ | \\ C_{22}H_{45}-N-CH_3 \\ | \\ CH_3 \end{array}\right]^{\oplus} Cl^{\ominus}$ | 2.26% |
| $\begin{array}{c} CH_3 \\ | \\ C_{18}H_{37}-N \longrightarrow O \\ | \\ CH_3 \end{array}$ | 2.74% |
| Cetyl alcohol | 0.88% |
| Glutamic acid | 0.27% |
| $Na_2SO_4$ | 0.50% |
| Color, flavor and antiseptic | adequate amount |
| Deionized water | 93.35% |

The so obtained hair-rinse liquid exhibited a pearly luster directly after the formulation and no change in the appearance was recognized after storage for 150 days at 0° C. or at 40° C. in a constant temperature bath. It revealed almost no irritative action and the hair rinsed with this liquid became soft, supple and sufficiently lustrous.

From these Examples, it has been made clear that the hair-rinse liquids according to the present invention exhibit a stable pearly luster without causing irritation and thus have excellent advantages.

What is claimed is:
1. A hair-rinse liquid with pearly luster comprising
Component A: a cationic surface active agent expressed by the general formula (I), as given below,
Component B: an amine oxide represented by the general formula (II), as given below,
Component C: an amino acid having an isoelectric point not higher than 7 and
Component D: a salt of an alkali metal or alkaline earth metal,
wherein the weight ratio of A:B:C:D is 1:[0.1–10]:[0.01–2]:9 0.01–2],

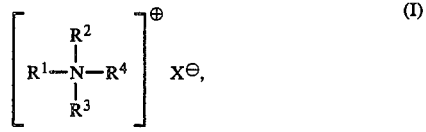

wherein $R^1$, $R^2$, $R^3$ and $R^4$ each represent a hydrocarbon group or a hydroxyalkyl group having 1–24 carbon atoms, which are identical to or different from each other, wherein the sum of the carbon atoms in each formula is within the range of 16–45, and X denotes a halogen atom.

2. A hair-rinse liquid with pearly luster according to claim 1, wherein $R^1$, $R^2$, $R^3$ and $R^4$ in the general formulae (I) and (II) each are selected from the group consisting of methyl, ethyl, propyl, isopropyl, allyl, butyl, isobutyl, tert-butyl, amyl, isoamyl, hexyl, heptyl, octyl, 2-ethylhexyl, nonyl, decyl, undecyl, lauryl, tridecyl, myristyl, cetyl, isocetyl, stearyl, isostearyl, oleyl, octyldodecyl, behenyl, docosenyl, decyltetradecyl, benzyl, hydroxyethyl, hydroxypropyl, hydroxybutyl and 2,3-dihydroxypropyl.

3. A hair-rinse liquid according to claim 1, wherein X in the general formula (I) is one or more halogen atoms selected from the group consisting of chlorine and bromine.

4. A hair-rinse liquid according to claim 1, wherein the component A is one or more cationic surface active agents selected from the group consisting of trimethyl cetylammonium chloride, trimethyl stearylammonium chloride, trimethyl behenylammonium chloride, trimethyl docosenylammonium chloride, dimethyl dicetylammonium chloride, dimethyl distearylammonium chloride, trimethyl octyldodecylammonium chloride and trimethyl decyltetradecylammonium chloride.

5. A hair-rinse liquid according to claim 1, wherein the component B is one or more amine oxides selected from the group consisting of N,N-dimethyl cetylamine oxide, N,N-dimethyl stearylamine oxide, N,N-di-(2-hydroxyethyl)stearylamine oxide, N-methyl distearylamine oxide, N,N-dimethyl behenylamine oxide, N,N-dimethyl docosenylamine oxide, N,N-dimethyl octyldodecylamine oxide and N,N-dimethyl decyltetradecylamine oxide.

6. A hair-rinse liquid according to claim 1, wherein the component C is one or more amino acids selected from the group consisting of glycine, alanine, valine, leucine, isoleucine, serine, threonine, phenylalanine, tyrosine, triptophane, cysteine, cystine, methionine, proline, hydroxyproline, asparaginic acid, glutamic acid, asparagine and glutamine.

7. A hair-rinse liquid according to claim 1, wherein the component D is one or more salts selected from the group consisting of those of sodium, potassium, magnesium and calcium with hydrochloric acid, sulfuric acid and phosphoric acid and alums.

* * * * *